United States Patent
Sheinker et al.

(10) Patent No.: US 9,891,291 B2
(45) Date of Patent: Feb. 13, 2018

(54) MAGNETIC TRACKING SYSTEM

(75) Inventors: Arie Sheinker, Herzeliya (IL); Boris Ginzburg, Rehovot (IL); Nizan Salomonski, Nes Ziona (IL)

(73) Assignee: Soreq Nuclear Research Center, Yavne (IL)

( * ) Notice: Subject to any disclaimer, the term of this patent is extended or adjusted under 35 U.S.C. 154(b) by 383 days.

(21) Appl. No.: 14/236,636

(22) PCT Filed: Aug. 1, 2012

(86) PCT No.: PCT/IB2012/053926
§ 371 (c)(1),
(2), (4) Date: Apr. 8, 2014

(87) PCT Pub. No.: WO2013/018038
PCT Pub. Date: Feb. 7, 2013

(65) Prior Publication Data
US 2014/0239943 A1    Aug. 28, 2014

Related U.S. Application Data

(60) Provisional application No. 61/513,688, filed on Aug. 1, 2011.

(51) Int. Cl.
*G01R 33/02* (2006.01)
*A61B 5/06* (2006.01)
(Continued)

(52) U.S. Cl.
CPC .............. *G01R 33/02* (2013.01); *A61B 5/062* (2013.01); *G01B 7/003* (2013.01); *G01B 7/004* (2013.01)

(58) Field of Classification Search
CPC ................................ G01D 1/00; G01D 5/2066
(Continued)

(56) References Cited

U.S. PATENT DOCUMENTS 4,314,251 A    2/1982   Raab et al.
4,710,708 A   12/1987   Rorden et al.
(Continued)

FOREIGN PATENT DOCUMENTS

DE    102009035948    9/2009
WO      2009035645    3/2009

OTHER PUBLICATIONS

International Search Report for PCT/IB2012/053926 dated Dec. 10, 2012.
(Continued)

*Primary Examiner* — Vinh Nguyen
(74) *Attorney, Agent, or Firm* — A.C. Entis-IP Ltd.

(57) ABSTRACT

Apparatus for determining a location of a target, the apparatus comprising: first and second magnetic dipole beacons positioned at substantially a same spatial location having respectively first and second time dependent magnetic moments oriented in different directions that generate first and second magnetic fields having different time dependencies; at least one magnetic field sensor coil located at the location of the target that generates signals responsive to the first and second magnetic fields; and circuitry that receives the signals generated by the at least one sensor coil and processes the signals responsive to the different time dependencies of the magnetic fields to determine a location of the at least one sensor coil and thereby the target.

17 Claims, 3 Drawing Sheets

(51) Int. Cl.
*G01B 7/004* (2006.01)
*G01B 7/00* (2006.01)

(58) Field of Classification Search
USPC .... 324/207.17, 200, 207.11, 207.13, 207.15, 324/207.16
See application file for complete search history.

(56) References Cited

U.S. PATENT DOCUMENTS

| | | | | |
|---|---|---|---|---|
| 4,808,923 | A * | 2/1989 | Posseme | G01R 33/00 324/207.17 |
| 5,966,013 | A * | 10/1999 | Hagiwara | G01V 3/38 324/335 |
| 5,999,883 | A | 12/1999 | Gupta et al. | |
| 6,073,043 | A | 6/2000 | Schneider | |
| 6,184,685 | B1 * | 2/2001 | Paulk | G01V 3/30 324/338 |
| 7,015,859 | B2 * | 3/2006 | Anderson | A61B 5/06 342/450 |
| 7,096,148 | B2 * | 8/2006 | Anderson | A61B 5/06 324/207.17 |
| 7,624,816 | B2 | 12/2009 | Cole et al. | |
| 7,728,595 | B2 | 6/2010 | Brune et al. | |
| 7,788,060 | B2 | 8/2010 | Schneider | |
| 7,794,407 | B2 | 9/2010 | Rothenberg | |
| 7,834,621 | B2 | 11/2010 | Anderson | |
| 7,898,494 | B2 | 3/2011 | Brune et al. | |
| 7,911,202 | B2 | 3/2011 | Anderson | |
| 8,072,220 | B2 * | 12/2011 | Dolgin | G01C 21/165 324/228 |
| 8,121,812 | B2 * | 2/2012 | Higgins | A61B 5/06 324/207.17 |
| 8,131,342 | B2 * | 3/2012 | Anderson | A61B 5/06 324/207.12 |
| 8,296,113 | B2 * | 10/2012 | San Martin | E21B 47/02216 702/7 |
| 9,002,437 | B2 * | 4/2015 | Yaroshenko | A61B 5/062 600/424 |
| 2006/0242099 | A1 * | 10/2006 | Chen | G06N 5/046 706/47 |
| 2006/0244454 | A1 | 11/2006 | Gard et al. | |
| 2006/0247511 | A1 * | 11/2006 | Anderson | A61B 5/06 600/407 |
| 2007/0055125 | A1 * | 3/2007 | Anderson | A61B 5/06 600/407 |
| 2007/0299623 | A1 | 12/2007 | Gandelsman et al. | |
| 2008/0036652 | A1 | 2/2008 | Shore et al. | |
| 2010/0271012 | A1 | 10/2010 | Patterson et al. | |
| 2012/0215475 | A1 * | 8/2012 | Rutledge | G05G 9/047 702/94 |
| 2012/0275780 | A1 * | 11/2012 | Hueda | H04L 25/03292 398/25 |

OTHER PUBLICATIONS

H. Kenneth Sacks,Electromagnetic Technique for Locating Boreholes; Report of Investigations 8302, United States Department of the Interior; Bureau of Mines Report of Investigations 1978.

"Stolar Research Achieves Wireless Communication for Locating Trapped Miners", Press Release Dec. 13, 2010; Stolar Research Corporation (Stolar) and the National Institute for Occupational Safety and Health (NIOSH): downloaded Feb. 3, 2014 from : http://www.coalzoom.com/article.cfm?articleid=975.

Extended European Search Report dated Feb. 20, 2015 for corresponding European application 12819450.3.

* cited by examiner

MAGNETIC TRACKING SYSTEM

RELATED APPLICATIONS

The present application is a US National Phase of PCT Application No. PCT/IB2012/053926, filed on Aug. 1, 2012, and claiming benefit under 35 U.S.C. 119(e) from U.S. provisional application 61/513,688 filed on Aug. 1, 2011, the disclosure of which is incorporated herein by reference.

TECHNICAL FIELD

Embodiments of the invention relate to locating an object using a magnetic field.

BACKGROUND

Different wireless location technologies and systems for determining a location of a mobile transmitter or receiver of electromagnetic waves, and thereby of a person or object, carrying or mounted with the transmitter or receiver are known. Among well known and ubiquitous systems that provide "tracking" services that determine locations for people and objects are, by way of example, the mobile phone network systems and global navigation satellite systems, of which the global positioning system (GPS) is perhaps the best known. For convenience of discussion, a transmitter and/or receiver, and/or a device in which it is housed, and/or its bearer, for which a location technology or system, hereinafter also a tracking system or tracking technology, determines locations may be distinguished as being a "target", used as a modifier or noun, of the tracking technology or system.

In the GPS tracking system, a GPS receiver, such as is commonly available for locating vehicles and persons, receives electromagnetic waves encoding synchronized clock signals from at least three GPS satellites. The clock signals are used to determine transit times of the electromagnetic waves from the satellites. The speed of light and transit times from the satellites are used to determine where on the face of the globe the receiver, and thereby the person or object bearing the receiver, is located. Mobile phone networks use signals transmitted by synchronized base station transmitters from different cells in the network to mobile terminals, such as mobile phones, personal digital assistants (PDA), and laptop computers, to track locations of the terminals. Locations of a mobile terminal may be provided responsive to differences in time of arrival, or differences in strength, of signals transmitted to the terminal by the base station transmitters.

It is noted that whereas in the above discussion, a single "target" receiver is described as being located by a tracking system responsive to electromagnetic signals transmitted from a plurality of transmitters, location technologies are of course not limited to locating a receiver using signals from a plurality of transmitters. Location technologies may generally be used in "reverse", with a single transmitter transmitting signals to three or four receivers to provide a location for the transmitter.

In general, functioning of wireless tracking systems, in determining locations of targets responsive to transmission of electromagnetic waves, is adversely affected by objects, terrain features, and/or weather artifacts that interfere with propagation of the waves. For example, most of the systems are adversely affected by "multipath signaling". In multipath signaling, energy from a same signal transmitted by a transmitter to a receiver is reflected from, or refracted by, objects, terrain features, and/or atmospheric artifacts present in a path along which the energy propagates so that portions of the energy travel by more than one path to the receiver. Different amounts of energy from the same signal therefore arrive at the receiver at different times. As a result, signal fidelity, and measurements of signal transit times and/or signal strength, may be compromised. Accuracy of locations provided by mobile phone systems are often substantially degraded by multipath effects. And, whereas GPS based location systems can be configured to provide determinations of locations of a receiver that are accurate to a few tens of centimeters, they generally do not function for locations of a receiver unless unencumbered lines of sight from the receiver location to at least three GPS satellites is available.

Tracking systems that use low frequency magnetic fields have been developed for locating a target under conditions for which masking or shielding of electromagnetic waves by objects, terrain features, and/or atmospheric artifacts make locating the target using electromagnetic wave tracking systems unreliable. Static and low frequency magnetic fields are substantially less affected by common masking or shielding artifacts than are electromagnetic waves. For example, magnetic tracking systems may be used to locate miners in mines and drilling rig drill tips in bore holes.

SUMMARY

An embodiment of the invention relates to providing a magnetic tracking system, hereinafter also referred to as a "MagneLoc" system or "MagneLoc", comprising a relatively simple configuration of magnetic dipole beacons that provide a low frequency magnetic field in a region of interest (ROI). The MagneLoc system may provide a location for a target in the ROI using a relatively simple algorithm that provides closed-form expressions for coordinates of the location of the target as a function of magnitude and direction of the field at the target.

In an embodiment of the invention, the magnetic beacons comprise first and second magnetic dipole beacons having, optionally orthogonal, magnetic moments that are located at substantially a same location and generate time dependent magnetic fields at relatively low first and second frequencies respectively. In an embodiment of the invention, the magnetic beacons comprise first and second magnetic dipole beacons at first and second locations respectively having magnetic moments that are substantially parallel and optionally, substantially perpendicular to a line that joins the first and second locations. In an embodiment of the invention the magnetic beacons generate time dependent magnetic fields at different frequencies.

An embodiment of the invention relates to a providing a MagneLoc system that comprises at least one magnetic dipole beacon that generates a magnetic field in a ROI, and a map of the magnetic field in the ROI. The map includes information that defines the magnetic field for each sub-region of a plurality of sub-regions in the ROI into which the ROI is partitioned. The target is determined to be located in that sub-region of the ROI for which the magnetic field associated with the sub-region by the map most closely matches a measurement of the magnetic field at the location of the target. Closeness of match is determined using any of various suitable metrics.

There is therefore provided in accordance with an embodiment of the invention apparatus for determining a location of a target, the apparatus comprising: first and second magnetic dipole beacons positioned at substantially a same spatial location having respectively first and second time dependent magnetic moments oriented in different directions that generate first and second magnetic fields having different time dependencies; at least one magnetic field sensor coil located at the location of the target that generates signals responsive to the first and second magnetic fields; and circuitry that receives the signals generated by the at least one sensor coil and processes the signals responsive to the different time dependencies of the magnetic fields to determine a location of the at least one sensor coil and thereby the target.

Optionally, the first and second magnetic beacons comprise first and second excitation coils respectively that generate the first and second magnetic moments, and a separation distance between the magnetic beacons is less than or equal to about a maximum dimension of a characteristic cross section of a largest of the first and second excitation coils. Optionally, the separation distance is less than or equal to about 0.5 of the maximum cross section dimension.

Optionally, the separation distance is less than or equal to about 0.1 of the maximum cross section dimension.

In an embodiment of the invention, the first and second magnetic moments vary harmonically in time with different characteristic frequencies. Optionally, at least one of the characteristic frequencies is less than about 1,000 Hz.

In an embodiment of the invention, the amplitudes of the time dependence of the first and second magnetic moments are substantially equal. In an embodiment of the invention, the first and second magnetic moments are substantially orthogonal. Optionally, the first and second magnetic moments are substantially coplanar.

In an embodiment of the invention, the at least one sensor coil comprises first and second sensor coils having first and second coil axes respectively. Optionally, the first sensor coil axis is parallel to one of the first and second magnetic moments. Additionally or alternatively, the first and second sensor coil axes are orthogonal.

In an embodiment of the invention, the circuitry processes the signals to determine a vector component of an amplitude of each of the first and second magnetic fields and uses the components to determine the location of the target. Optionally, the circuitry determines a ratio of different components of the first magnetic field and uses the ratio to determine the location of the target. The circuitry optionally determines a difference between a spatial component of the first magnetic field and a different spatial component of the second magnetic field and uses the difference to determine the location of the target. In an embodiment of the invention, the circuitry evaluates a closed-form expression that determines a spatial coordinate of the at least one coil as a function of the ratio and the difference to determine the location of the target.

There is further provided in accordance with an embodiment of the invention, a method of determining a location of a target, the method comprising: generating magnetic moments located at a same location and having different directions to produce a magnetic field; generating signals responsive to the magnetic field at the location of the target; and using the signals to determine the location of the target. Optionally, using the signals comprising determining components of the magnetic field. Optionally the method comprises evaluating a closed-form expression that provides a spatial coordinate of the target as a function of the components of the magnetic field.

There is further provided in accordance with an embodiment of the invention, apparatus for determining a location of a target, the apparatus comprising: first and second magnetic dipole beacons located at different spatial locations having respectively first and second substantially parallel time dependent magnetic moments that generate first and second magnetic fields having different time dependencies; at least one magnetic field sensor coil located at the location of the target that generates signals responsive to the first and second magnetic fields; and circuitry that receives the signals generated by the at least one sensor coil and processes the signals responsive to the different time dependencies of the magnetic fields to evaluate a closed-form expression that determines a spatial coordinate of the at least one sensor coil and thereby of the target.

There is further provided in accordance with an embodiment of the invention, apparatus for determining a location of a target, the apparatus comprising: a plurality of dipole beacons located at different spatial locations having time different dependent magnetic moments that generate a magnetic field; a map of values of the magnetic field as a function of spatial position; at least one magnetic field sensor coil located at the location of the target that generates signals responsive to the magnetic field; and circuitry that receives the signals generated by the at least one sensor coil and processes the signals responsive to their respective time dependencies to determine the magnetic field at the location of the target and compares the determined magnetic field to values of the magnetic field provided by the map to determine a location for the target.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF FIGURES

Non-limiting examples of embodiments of the invention are described below with reference to figures attached hereto that are listed following this paragraph. Identical structures, elements or parts that appear in more than one figure are generally labeled with a same label in all the figures in which they appear. Labels labeling an icon representing a component or feature in a figure may be used to refer to and identify the component or feature represented by the icon. Dimensions of components and features shown in the figures are chosen for convenience and clarity of presentation and are not necessarily shown to scale.

DETAILED DESCRIPTION

Figure 1:
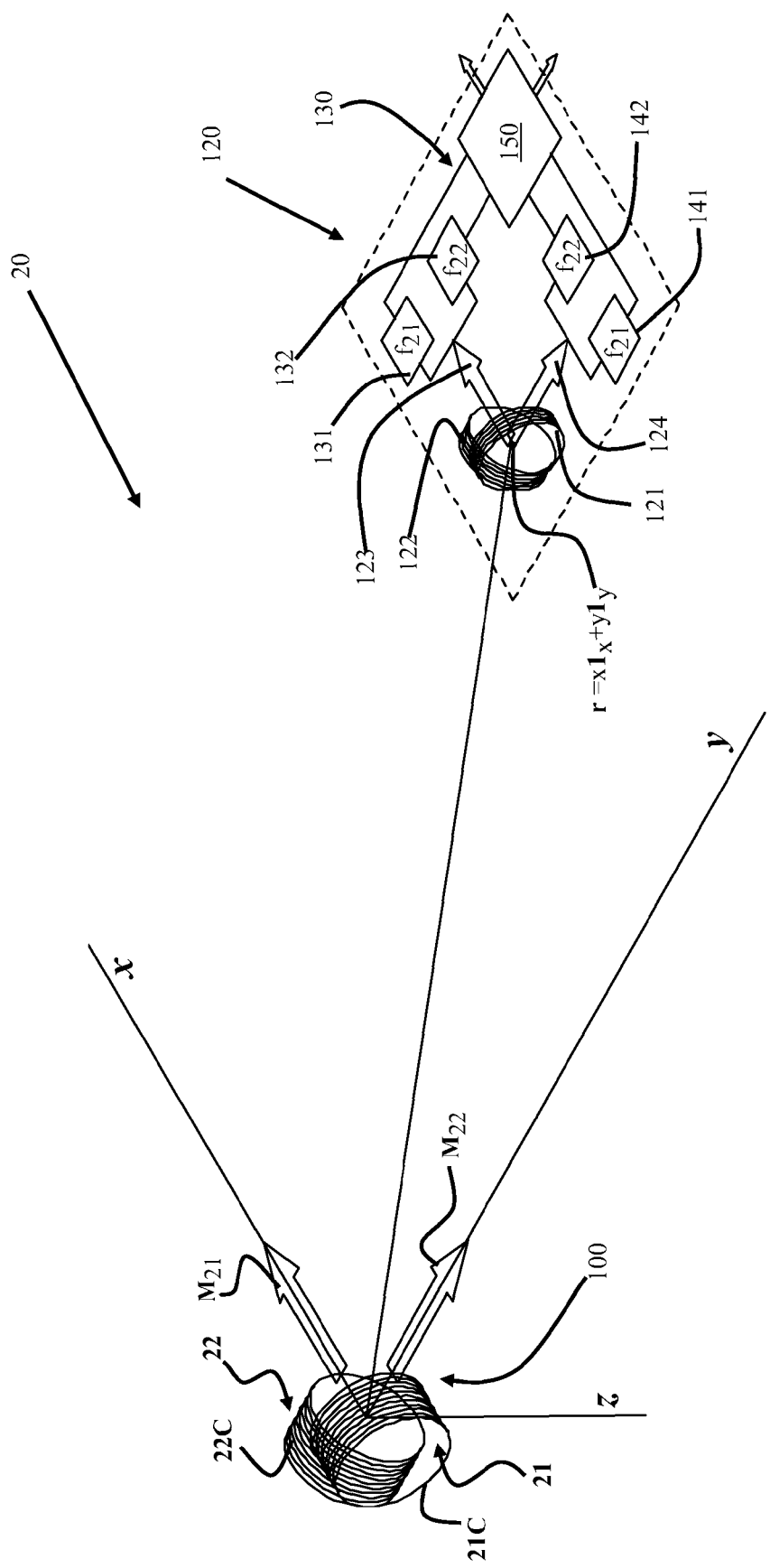
FIG. 1 schematically shows a MagneLoc tracker comprising two magnetic dipole beacons located at a same location tracking a target, in accordance with an embodiment of the invention.

FIG. 1 schematically shows a MagneLoc tracker system 20 comprising first and second magnetic dipole beacons 21 and 22 having excitation coils 21C and 22C, which are located substantially at a same location at an origin of a Cartesian coordinate system 100, in accordance with an embodiment of the invention. A magnetic moment $M_{21}$ of beacon 21 lies along the x axis of coordinate system 100 and is schematically represented by a block arrow labeled $M_{21}$. A magnetic moment $M_{22}$ of beacon 22 lies optionally along the y axis of the coordinate system and is schematically represented by a block arrow labeled $M_{21}$. MagneLoc tracker 20 comprises, and is schematically shown tracking, a target 120.

A location of a magnetic moment of a magnetic dipole beacon is assumed to define and be coincident with the location of the magnetic beacon and an excitation coil of the magnetic beacon that generates the magnetic moment. For convenience of presentation, bold faced text is used to indicate a vector. Unit vectors along the x, y, and z axis of coordinate system 100 are represented by $1_x$, $1_y$, and $1_z$ respectively.

In an embodiment of the invention, currents in dipole beacons 21 and 22, are controlled so that magnetic moments $M_{21}$ and $M_{22}$ of the beacons are time dependent, optionally varying harmonically in time with characteristic frequencies $f_{21}$ and $f_{22}$ respectively, and have a same amplitude "$M_o$".

For the above specifications, the magnetic moments may be written:

$$M_{21} = M_o 1_x \cos(2\pi f_{21} t + \varphi_{21}); \qquad 1)$$

and $$M_{22} = M_o 1_y \cos(2\pi f_{22} t + \varphi_{22}); \qquad 2)$$

where $\varphi_{21}$ and $\varphi_{22}$ are phase angles.

The harmonically varying magnetic moments $M_{21}$ and $M_{22}$ generate time dependent magnetic fields $B_{21}(r,t)$ and $B_{22}(r,t)$, which at a location $r = x1_x + y1_y$ on the xy-plane may be written:

$$B_{21}(r,t) = (\mu_o/4\pi) M_o [(3x^2 r^{-5} - r^{-3}) 1_x + (3xy r^{-5}) 1_y] \cos(2\pi f_{21} t + \varphi_{21}), \qquad 3)$$

and $$B_{22}(r,t) = (\mu_o/4\pi) M_o [(3xy r^{-5}) 1_x + (3x^2 r^{-5} - r^{-5}) 1_y] \cos(2\pi f_{22} t + \varphi_{22}). \qquad 4)$$

Target 120 is shown located at location $r = x1_x + y1_y$ and optionally comprises sensor coils 121 and 122 that generate potentials responsive to changes in a magnetic field that passes through the coils. Sensor coils 121 and 122 have axes, represented by block arrows 123 and 124 respectively, that are optionally perpendicular to each other and parallel respectively to magnetic moments $M_{21}$ and $M_{22}$. Alignment of axes 123 and 124 with magnetic moments $M_{21}$ and $M_{22}$ is optionally accomplished by aligning the magnetic moments and axes relative to the earth's magnetic field, optionally using a magnetic compass. Optionally, alignment is performed by aligning sensor coils 121 and 122 to a magnetic field generated by beacons 21 and/or 22. For example, the sensor coils may be aligned first to a magnetic field generated by only one of beacons 21 and 22 and then to a magnetic field generated by only the other of the beacons. Once aligned, continued alignment may be monitored and/or maintained responsive to signals generated by an accelerometer, gyroscope, and/or magnetic compass (not shown).

Current or voltage generated by sensor coil 121 responsive to a time varying magnetic field that passes through the sensor coils is input to lock-in amplifiers 131 and 132 comprised in circuitry 130. Lock-in amplifier 131 is tuned to frequency $f_{21}$ of beacon 21 and lock-in amplifier 132 is tuned to frequency $f_{22}$ of beacon 22. Lock-in amplifiers 131 and 132 generate DC signals responsive to the input from sensor coil 121 that are proportional to the amplitudes of the $1_x$ components of the magnetic fields generated at a location of sensor coil 121 by beacons 21 and 22 respectively.

The vector amplitudes of the magnetic fields generated by beacons 21 and 22 at location $r = x1_x + y1_y$ of target 120 are:

$$B_{21}(r) = (\mu_o/4\pi) M_o [(3x^2 r^{-5} - r^{-3}) 1_x + (3xy r^{-5}) 1_y]; \qquad 5)$$

and $$B_{22}(r) = (\mu_o/4\pi) M_o [(3xy r^{-5}) 1_x + (3x^2 r^{-5} - r^{-5}) 1_y] \qquad 6)$$

respectively.

Lock-in amplifiers 131 and 132 therefore provide DC signals proportional to the scalar products $B_{21}(r) \cdot 1_x$ and $B_{22}(r) \cdot 1_x$ respectively.

Similarly, current or voltage generated by sensor coil 122 is input to lock-in amplifiers 141 and 142 that are tuned to frequencies $f_{21}$ and $f_{22}$ respectively. Lock-in amplifiers 141 and 142 generate DC signals responsive to the input from sensor coil 122 that are proportional to amplitudes of the $1_y$ components of the magnetic fields generated by beacons 21 and 22 respectively at the location $r = x1_x + y1_y$ of sensor coil 122. Lock-in amplifiers 141 and 142 therefore provide DC signals proportional to the scalar products $B_{21}(r) \cdot 1_y$ and $B_{22}(r) \cdot 1_y$ respectively.

The signals generated by lock-in amplifiers 131, 132, 141, and 142 are optionally transmitted for processing to a processor 150 optionally comprised in circuitry 130. In an embodiment of the invention processor 150 uses inputs from lock-in amplifiers 131 and 142 to determine a ratio $$a_{21} = B_{21}(r) \cdot 1_x / B_{21}(r) \cdot 1_y = x/y - (x^2 + y^2)/3xy. \qquad 7)$$

Ratio $a_{21}$ implies a quadratic equation that may be solved to provide a ratio $$k_{21} = x/y = 0.25[3a_{21} \pm (9a_{21}^2 + 8)^{1/2}]. \qquad 8)$$

The plus sign in equation 8) applies for situations in which coordinates x and y have a same sign. The minus sign applies when the coordinates have opposite signs.

Optionally, processor 150 uses signals provided by lock-in amplifiers 131 and 132 to determine a difference, $$\Delta Bxy = B_{21}(r) \cdot 1_x - B_{22}(r) \cdot 1_y = (\mu_o/4\pi) 3 M_o (x^2 - y^2) r^{-5}. \qquad 9)$$

Using equation 8) the expression for $\Delta Bxy$ may be written $$\Delta Bxy = (\mu_o/4\pi) 3 M_o (k_{21}^2 - 1) y^{-3} (k_{21}^2 + 1)^{-2.5}. \qquad 10)$$

In an embodiment of the invention, processor 150 determines values for the x and y coordinates of the location of target 120 in terms of the variables $k_{21}$ and $\Delta Bxy$ in accordance with expressions:

$$x = k_{21} [3(\mu_o/4\pi) M_o (k_{21}^2 - 1)(k_{21}^2 + 1)^{-2.5} (\Delta Bxy)^{-1}]^{1/3}; \qquad 11)$$

and $$y = [3(\mu_o/4\pi) M_o (k_{21}^2 - 1)(k_{21}^2 + 1)^{-2.5} (\Delta Bxy)^{-1}]^{1/3}. \qquad 12)$$

By way of numerical examples, a MagneLoc tracker in accordance with an embodiment of the invention similar to MagneLoc 20 may comprise beacons 21 and 22 having a magnetic moment amplitude $M_o$ greater than or equal to about 5 A-m² (ampere×square meters). Optionally, $M_o$ is greater than or equal to about 10 A-m² (ampere×square meters). Optionally, $M_o$ is greater than or equal to about 100 A-m². In an embodiment of the invention, at least one of frequencies $f_{21}$ and $f_{22}$ is a relatively low frequency. In an embodiment of the invention, at least one of the frequencies $f_{21}$ and $f_{22}$ is less than about 1,000 Hz. Optionally, at least one of the frequencies is less than about 750 Hz. Optionally, at least one of the frequencies is less than about 500 Hz. Optionally, a separation distance between locations of magnetic beacons 21 and 22 may be less than or equal to about a maximum dimension, such as a diameter or diagonal dimension, of a characteristic cross section of a largest of coils 21C and 22C. Optionally, the separation distance is less than or equal to about 0.5 of the maximum cross section dimension. In an embodiment of the invention, the separation distance is less than or equal to about 0.1 of the maximum cross section dimension.

An experimental MagneLoc tracker similar to MagneLoc 20 for which magnetic moment amplitude $M_o$ of beacons 21 and 22 was equal to about 10 A-m$^2$, $f_{21}$=630 Hz, and $f_{22}$=770 Hz, provided determinations of locations for target 120 having an error less than or equal to about 0.18 m (meters) in a rectangular ROI 10 m by 11 m. Magnetic dipole beacons 21 and 22 were substantially square, having a side dimension equal to about 1 m, and were located at a corner of the ROI and within about 0.8 m of each other. Lock in amplifiers 131, 132, 141 and 142 were tuned to frequencies $f_{21}$ and $f_{22}$ to an accuracy of about 0.001 Hz, and had cutoff frequencies equal to about 10 Hz.

By way of another numerical example, an experiment was conducted with a magnetic tracking system in accordance with an embodiment of the invention similar to MagneLoc 20 comprising magnetic dipole beacons having a magnetic moment amplitude, $M_o$, equal to about 700 A-m$^2$. At distances from the beacons equal to about 80 m, the system provided locations for a target similar to target 20 with an accuracy of about 1 m.

Whereas in the above description magnetic moment $M_{21}$ is substantially perpendicular to magnetic moment $M_{22}$, and axes 123 and 124 of sensor coils 121 and 122 are parallel respectively to $M_{21}$ and $M_{22}$, practice of the invention is not limited to configurations of a magnetic tracking system in which magnetic moments are orthogonal and/or sensor coils are parallel to the magnetic moments. Closed-form equations in accordance with an embodiment of the invention, modified for lack of orthogonality and/or lack of parallelism of beacon and/or sensor coils may be used to determine coordinates of a target provided by the magnetic tracking system.

For example, components $B_{21}(r) \cdot 1_x$ and $B_{21}(r) \cdot 1_y$ (equation 4) may be determined from measurements made by optionally two sensor coils having axes that are not orthogonal and for which neither sensor coil is either parallel or perpendicular to a magnetic moment $M_{21}$ that generates $B_{21}(r)$. Similarly, components $B_{22}(r) \cdot 1_x$ and $B_{22}(r) \cdot 1_y$ (equation 5) may be determined from measurements made by optionally two sensor coils having axes that are not orthogonal and for which neither sensor coil is either parallel or perpendicular to a magnetic moment $M_{22}$ that generates $B_{22}(r)$. Closed-form expressions similar to equations 10) and 11) may be used to determine coordinates x and y for a target.

It is further noted that whereas in the above description two sensor coils are used to determine components of $B_{21}(r)$ and $B_{22}(r)$, a single sensor coil or a plurality of sensor coils greater than two may be used to determine components of $B_{21}(r)$ and $B_{22}(r)$, in accordance with an embodiment of the invention. For example, a single sensor coil may be used and rotated to different orientations to determine components of $B_{21}(r)$ and $B_{22}(r)$.

Figure 2:
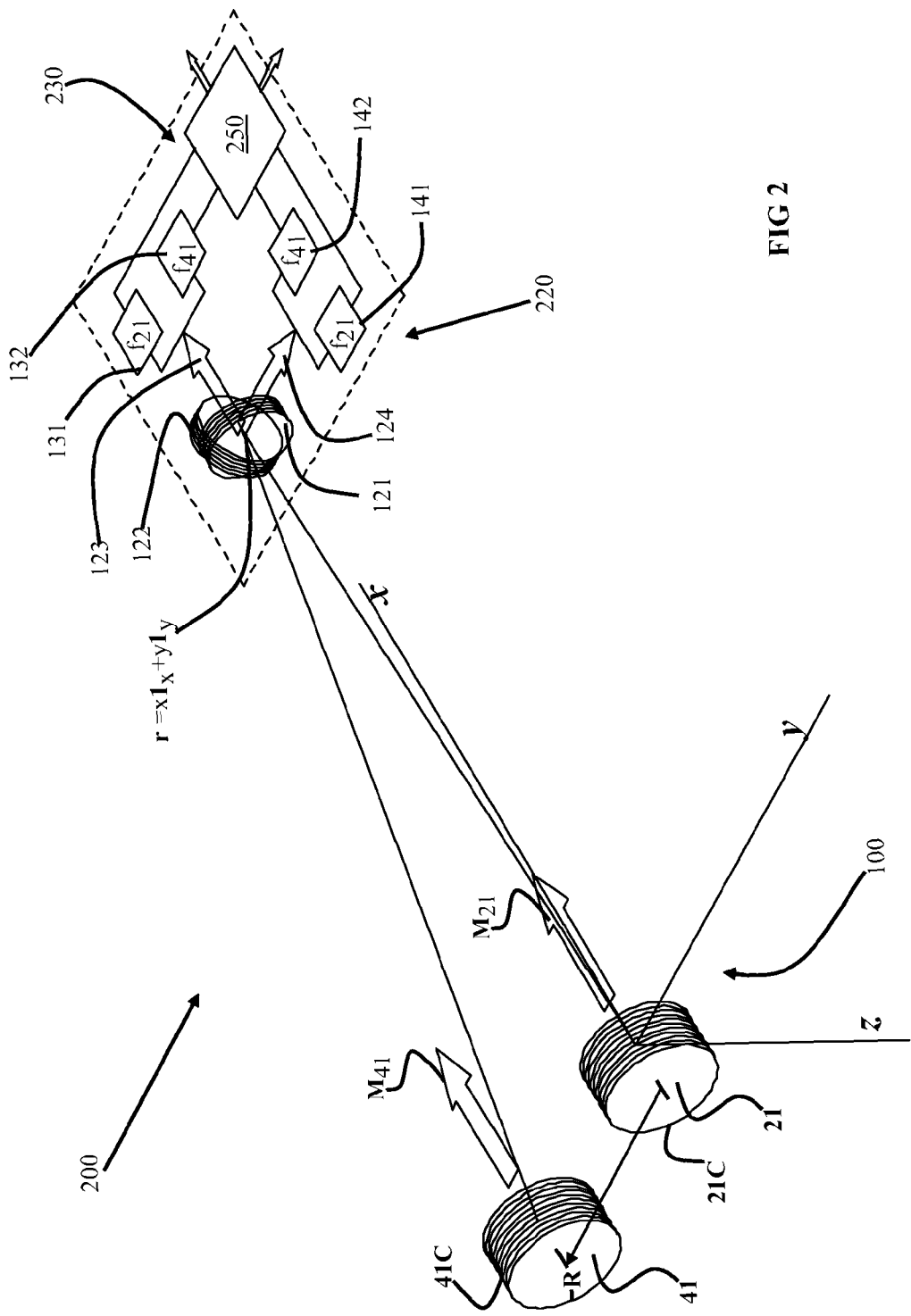
FIG. 2 schematically shows a MagneLoc tracker comprising two spaced apart magnetic dipole beacons tracking a target, in accordance with an embodiment of the invention.

FIG. 2 schematically shows another MagneLoc tracker 200, in accordance with an embodiment of the invention. MagneLoc tracker 200 optionally comprises magnetic dipole beacon 21, a magnetic dipole beacon 41, and a target 220. Magnetic beacons 21 and 41 comprise excitation coils 21C and 41C respectively.

Beacon 41 has a time dependent magnetic moment $M_{41}$ that is parallel to magnetic moment $M_{21}$, varies harmonically in time with a frequency $f_{41}$, and generates a corresponding, harmonically varying magnetic field $B_{41}(r,t)$. The magnetic moment of beacon 41 is schematically represented in FIG. 2 by a block arrow labeled $M_{41}$. Beacon 41 is displaced from beacon 21 by a separation distance R, optionally in the negative direction along the y axis of coordinate system 100. In an embodiment of the invention, R may be greater than a maximum cross section dimension, such as a diameter, or diagonal dimension, of a characteristic cross section of a largest of coils 21C and 41C. Optionally, R is greater than or equal to about twice the maximum cross section dimension. In an embodiment of the invention the separation distance is greater than or about equal to three times the maximum cross section dimension. Target 220 is optionally similar to target 120 except that it comprises circuitry 230 having lock-in amplifiers 132 and 142 tuned to frequency $f_{41}$ instead of frequency $f_{22}$ and a processor 250, which may process signals from the lock-in amplifiers differently than processor 150.

In an embodiment processor 250 determines ratios $a_{41}$ and $k_{41}$ similar to ratios $a_{21}$ and $k_{21}$ determined for beacon 21 shown in FIG. 1. In particular, $$a_{41}=B_{41}(r) \cdot 1_x/B_{41}(r) \cdot 1_y \qquad 13)$$

and $$k_{41}=x/(y+R)=0.25[3a_{41} \pm (9a_{41}^2+8)^{1/2}]. \qquad 14)$$

Processor 250 optionally determines x and y coordinates for location of target 220 in accordance with equations:

$$y=Rk_{41}(k_{21}-k_{41})^{-1}; \qquad 15)$$

and $$x=k_{41}(y+R). \qquad 16)$$

A simulation of operation of MagneLoc 200 similar to the simulation performed for MagneLoc 20, with beacons 21 and 41 (FIG. 2) having $M_o$ equal to about 10 A-m$^2$ and separated by a distance of about 3 m indicated that MagneLoc 200 could provide locations having an error equal to or less than about 0.1 m.

Embodiments of the invention are not limited to locating targets in two dimensions. For example, a MagneLoc tracker comprising three magnetic beacons and a target similar to targets 120 or 220, but including instead of two sensor coils three sensor coils having optionally orthogonal axes respectively in the $1_x$, $1_y$, and $1_z$ directions may be used to locate the target in three dimensions and provide x, y and z coordinates for the target.

Assume that the three magnetic beacons are positioned at locations (0,0,0), ($R_x$,0,$R_z$), and (0,$R_y$,0) respectively and have magnetic moments $M_o1_x$(0,0,0), $M_o1_x$($R_x$,0,$R_z$), and $M_o1_y$(0,$R_y$,0) that vary harmonically in time with frequencies $f_1$, $f_2$, and $f_3$. Let the magnetic fields that the magnetic moments generate be represented by $B_1(r,t)$, $B_2(r,t)$, and $B_3(r,t)$ respectively at a location r=x$1_x$+y$1_y$+z$1_z$ of the target. Let the amplitudes of the magnetic fields $B_1(r,t)$, $B_2(r,t)$, and $B_3(r,t)$ be represented by $B_1(r)$, $B_2(r)$, and $B_3(r)$ respectively. In accordance with an embodiment of the invention, an output of each of the target sensor coils is coupled to three lock-in amplifiers, each tuned to a different one of frequencies $f_1$, $f_2$, and $f_3$. The sensor coils and their associated lock-in amplifiers may therefore provide measurements of the $1_x$, $1_y$, and $1_z$ components of $B_1(r)$, $B_2(r)$, and $B_3(r)$. The location of the target may be determined in accordance with an embodiment of the invention in accordance the following expressions:

$$x = z(B_3(r) \cdot 1_x / B_3(r) \cdot 1_z); \qquad (17)$$

$$y = z(B_1(r) \cdot 1_y / B_1(r) \cdot 1_z); \qquad (18)$$

and $$z = R_x B_2(r) \cdot 1_y / [B_2(r) \cdot 1_z (B_2(r) \cdot 1_y / B_2(r) \cdot 1_z - B_1(r) \cdot 1_y / B_1(r) \cdot 1_z)]. \qquad (19)$$

Figure 3:
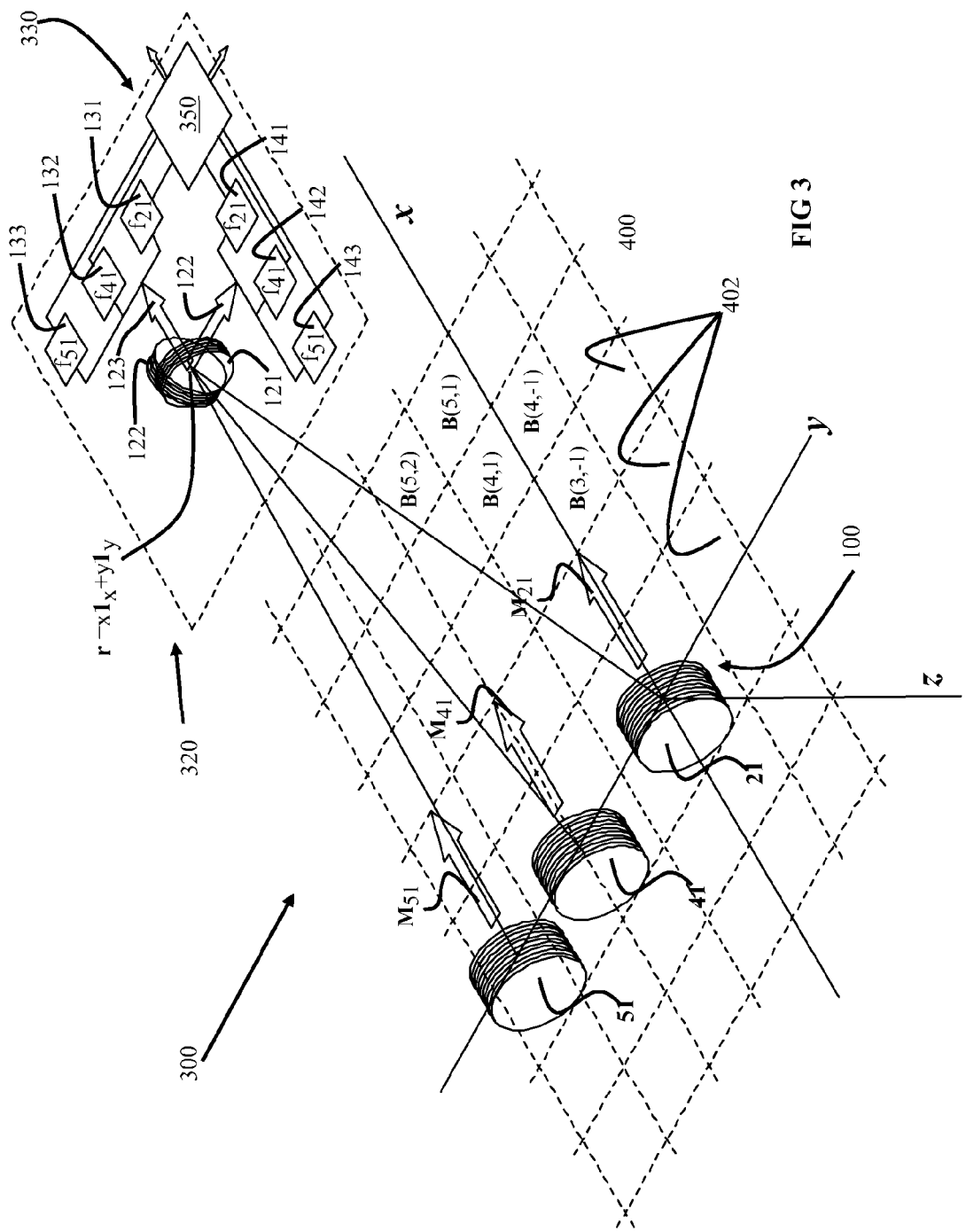
FIG. 3 schematically shows a MagneLoc tracker that uses a magnetic map to track a target, in accordance with an embodiment of the invention.

FIG. 3 schematically shows a MagneLoc tracker system 300 that uses a "magnetic map" of a magnetic field generated by at least one dipole beacon to track a target 320 in a region of interest 400, in accordance with an embodiment of the invention.

MagneLoc 300 comprises at least one dipole beacon having a magnetic moment parallel to the x-axis of coordinate system 100. By way of example, MagneLoc 300 comprises three dipole beacons 21, 41, and 51 optionally having their respective magnetic moments $M_{21}$, $M_{41}$ and $M_{51}$ parallel to the x-axis and coplanar. The magnetic moments vary harmonically with frequencies $f_{21}$, $f_{41}$, and $f_{51}$ respectively. Target 320 is similar to target 220 (FIG. 2) but comprises circuitry 330 having lock in amplifiers 143 and 133 that are tuned to frequency $f_{51}$ in addition to lock-in amplifiers that are tuned into frequencies $f_{21}$, $f_{41}$. Circuitry 330 optionally comprises a processor 350 that receives signals from the lock-in amplifiers 131, 132, 133, 141, 142, and 143, processes signals from the lock-in amplifiers using a magnetic map of a magnetic field generated by dipole beacons 21, 41, and 51 in ROI 400 to determine locations for target 320 in the ROI.

The magnetic map used by MagneLoc 300 comprises values for the magnetic field generated by magnetic moments $M_{21}$, $M_{41}$ and $M_{51}$ for each of a plurality of contiguous cells 402 into which ROI 400 is divided. In FIG. 3 by way of example, ROI 400 is a planar ROI coincident with the xy plane of coordinate system 100 and cells 402 are optionally square same size cells. Each cell 402 is identified by indices "i", and "j" that satisfy constraints $1 \leq i \leq I$ and $1 \leq j \leq J$ respectively, and define x and y spatial coordinates of the center of the cell. For example, the center of the (i,j)-th cell has x and y spatial coordinates, $$x(i) = (i - 0.5)\Delta$$

and $$y(j) = (j - 0.5)\Delta, \qquad (20)$$

where $\Delta$ is a length of a side of the cells.

The magnetic field associated with the (i,j)-th cell 402 is represented by $$B(i,j) = B_{21}(i,j) + B_{41}(i,j) + B_{51}(i,j), \qquad (21)$$

where $B_{21}(i,j)$, $B_{41}(i,j)$, and $B_{51}(i,j)$ are the magnetic fields generated at the center of the (i,j)-th cell by magnetic moments $M_{21}$, $M_{41}$ and $M_{51}$ respectively. $B(i,j)$ is indicated for some cells 402 in FIG. 3. Optionally, values defining the $B(i,j)$ are stored and associated with their corresponding indices (i,j) in a look-up table (LUT) in processor 350.

In accordance with an embodiment of the invention, to determine a location of target 320, processor 350 processes signals provided by lock-in amplifiers 131, 132, 133, 141, 142, and 143 to determine the magnetic field at the location of the target. Let the target location be represented by coordinates $(x_T, y_T)$ and the magnetic field at location $(x_T, y_T)$ be represented by $B_T$. In an embodiment of the invention, processor 350 determines coordinates $x_T, y_T$ for the target as the coordinates x(i), y(j) of the (i,j)-th cell for which a metric that provides a measure of a difference between $B_T$ and B(i,j) has a minimum.

By way of example, in an embodiment of the invention, processor 350 uses a metric equal to $|B_T - B(i,j)|$ to determine indices $i^*, j^*$ for which $|B_T - B(i,j)|$ is a minimum. In symbols $(i^*, j^*)$ satisfies the criterion, $$\{(i^*, j^*) | \min|B_T - B(i,j)|, \forall i,j\}. \qquad (22)$$

The processor then determines coordinates $x_T$, $y_T$ in accordance with an expression $$(x_T, y_T) = x(i^*), y(j^*). \qquad (21)$$

It is noted that a MagneLoc tracker that uses a magnetic map in accordance with an embodiment is not limited to square cells or a metric used in equation 18. For example, cells may be rectangular or hexagonal and a best agreement between $B_T$ and a B(i,j) may be searched for using a genetic algorithm or any other global search method. Furthermore, whereas cells 402 in FIG. 3 are planar, a MagneLoc tracker in accordance with an embodiment of the invention is not limited to planar cells locating an object in a planar ROI. For example, a MagneLoc tracker in accordance with an embodiment of the invention may operate to provide locations of a target in a three dimensional space partitioned into three dimensional, optionally cubic cells.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. Apparatus for determining a location of a target, the apparatus comprising:
   first and second magnetic dipole beacons positioned at substantially a same spatial location having respectively first and second time dependent magnetic moments oriented in different directions that generate first and second magnetic fields having different time dependencies;
   at least one magnetic field sensor coil located at the location of the target that generates signals responsive to the first and second magnetic fields; and
   circuitry that receives the signals generated by the at least one magnetic field sensor coil and processes the signals responsive to the different time dependencies of the first and second magnetic fields to determine spatial coordinates of a location of the at least one sensor coil and thereby the target as equal to values of respective closed form expressions, each closed form expression a function of a ratio between different components of a same magnetic field of the first and second magnetic fields and a magnitude of a difference between magnitudes of different components of the first and second magnetic fields.

2. The apparatus according to claim 1 wherein the first and second magnetic dipole beacons comprise first and second excitation coils respectively that generate the first and second time dependent magnetic moments, and a separation distance between the first and second magnetic dipole beacons is less than or equal to about a maximum dimension of a characteristic cross section of a largest of the first and second excitation coils.

3. The apparatus according to claim 2 wherein the separation distance is less than or equal to about 0.5 of the maximum cross section dimension.

4. The apparatus according to claim 3 wherein the separation distance is less than or equal to about 0.1 of the maximum cross section dimension.

5. The apparatus according to claim 1 wherein the first and second magnetic moments vary harmonically in time with different characteristic frequencies.

6. The apparatus according to claim 5 wherein, at least one of the characteristic frequencies is less than about 1,000 Hz.

7. The apparatus according to claim 5 wherein the amplitudes of the time dependence of the first and second magnetic moments are substantially equal.

8. The apparatus according to claim 1 wherein the first and second time dependent magnetic moments are substantially orthogonal.

9. The apparatus according to claim 8 wherein the first and second time dependent magnetic moments are substantially coplanar.

10. The apparatus according to claim 1 wherein the at least one magnetic field sensor coil comprises first and second sensor coils having first and second coil axes respectively.

11. The apparatus according to claim 10 wherein the first sensor coil axis is parallel to one of the first and second time dependent magnetic moments.

12. The apparatus according to claim 10 wherein the first and second sensor coil axes are orthogonal.

13. The apparatus according to claim 1 wherein the circuitry evaluates a closed-form expression of the respective closed form expressions that determines a spatial coordinate of the at least one magnetic sensor coil as a function of the ratio and the difference to determine the location of the target.

14. The apparatus according to claim 1 wherein the spatial coordinates of the at least one magnetic field sensor coil are determined, respectively, as $$x = k_{21}[3(\mu o/4\pi)M_o(k_{21}^2-1)(k_{21}^2+1)^{-2.5}(\Delta Bxy)^{-1}]^{1/3},$$
and
$$y = [3(\mu o/4\pi)M_o(k_{21}^2-1)(k_{21}^2+1)^{-2.5}(\Delta Bxy)^{-1}]^{1/3},$$

where:
$k_{21}$ is defined as $0.25[3a_{21} \pm (9a_{21}^2+8)^{1/2}]$ where $a_{21}$ is evaluated as $x/y-(x^2+y^2)/3xy$;
$\Delta Bxy$ is defined as $(\mu o/4\pi)3M_o(k_{21}^2-1)y^{-3}(k_2^{12}+1)^{-2.5}$;
$\mu o$ is the magnetic permeability; and
$M_o$ is the magnetic moment.

15. Apparatus for determining a location of a target, the apparatus comprising:
first and second magnetic dipole beacons positioned at substantially a same spatial location having respectively first and second time dependent magnetic moments oriented in different directions that generate first and second magnetic fields having different time dependencies;
at least one magnetic field sensor coil located at the location of the target that generates signals responsive to the first and second time dependent magnetic fields and wherein a magnetic field sensor coil of the at least one magnetic field sensor coil is maintained parallel to one of the first and second magnetic moments; and
circuitry that receives the signals generated by the at least one magnetic field sensor coil and processes the signals responsive to the different time dependencies of the magnetic fields to determine a location of the at least one sensor coil and thereby the target.

16. Apparatus for determining a location of a target, the apparatus comprising:
first and second magnetic dipole beacons comprising first and second excitation coils respectively positioned at substantially a same spatial location having respectively first and second time dependent magnetic moments oriented in different directions that generate first and second magnetic fields having different time dependencies and wherein a separation distance between the first and second magnetic beacons is less than or equal to about a maximum dimension of a characteristic cross section of a largest of the first and second excitation coils;
at least one magnetic field sensor coil located at the location of the target that generates signals responsive to the first and second magnetic fields; and
circuitry that receives the signals generated by the at least one magnetic field sensor coil and processes the signals responsive to the different time dependencies of the first and second magnetic fields to determine a location of the at least one magnetic field sensor coil and thereby the target.

17. The apparatus according to claim 16 wherein the separation distance is less than or equal to about 0.1 of the maximum dimension of the characteristic cross section of the largest of the first and second excitation coils.

* * * * *